United States Patent [19]
Sutton et al.

[11] Patent Number: 6,022,525
[45] Date of Patent: *Feb. 8, 2000

[54] PREPARATION OF DIAGNOSTIC AGENTS

[75] Inventors: Andrew D. Sutton, Ruddington; Richard A. Johnson, West Bridgford; Peter J. Senior, Near Melbourne; David Heath, Nottingham, all of United Kingdom

[73] Assignee: Quadrant Healthcare (UK) Limited, United Kingdom

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/517,590

[22] Filed: Aug. 22, 1995

Related U.S. Application Data

[63] Continuation of application No. 07/956,875, filed as application No. PCT/GB92/00643, Apr. 10, 1992, Pat. No. 5,518,709.

[30] Foreign Application Priority Data

Apr. 10, 1991 [GB] United Kingdom ............... 91 07628

[51] Int. Cl.$^7$ ............... A61K 49/00; A61B 8/00; A61B 8/02

[52] U.S. Cl. ............ 424/9.52; 106/122; 106/646; 252/363.5; 264/4.3; 264/4.6; 516/928; 600/443; 600/453; 600/458

[58] Field of Search .................... 264/4.3, 4.6; 424/9.52; 428/402.2; 128/660.01, 660.02, 660.05, 661.04, 662.02; 530/363; 106/646, 122; 600/443, 458

[56] References Cited

U.S. PATENT DOCUMENTS

| | | | |
|---|---|---|---|
| 2,797,201 | 6/1957 | Veatch et al. | 260/2.5 |
| 2,805,977 | 9/1957 | Robinson et al. | 424/499 |
| 3,043,782 | 7/1962 | Jensen | 427/213.33 X |
| 3,501,419 | 3/1970 | Bridgeford | 260/2.5 |
| 3,565,559 | 2/1971 | Sato et al. | 424/492 |
| 3,781,230 | 12/1973 | Vassiliades et al. | 260/2.5 |
| 3,863,004 | 1/1975 | Wolfnagel . | |
| 3,960,583 | 6/1976 | Netting et al. | 106/122 |
| 4,089,800 | 5/1978 | Temple | 252/316 |
| 4,102,806 | 7/1978 | Kondo et al. | 252/316 |

(List continued on next page.)

FOREIGN PATENT DOCUMENTS

| | | |
|---|---|---|
| 649 996 | 10/1991 | Australia . |
| 0 052 575 | 5/1982 | European Pat. Off. . |
| 0 091 555 | 10/1983 | European Pat. Off. . |
| 0 131 540 | 1/1985 | European Pat. Off. . |
| 0 224 934 | 6/1987 | European Pat. Off. . |
| 0 234 938 | 7/1989 | European Pat. Off. . |
| 0 327 490 | 8/1989 | European Pat. Off. . |
| 0 381 543 | 8/1990 | European Pat. Off. . |
| 0 458 079 | 11/1991 | European Pat. Off. . |
| 0 458 745 | 11/1991 | European Pat. Off. . |
| 0 494 615 | 7/1992 | European Pat. Off. . |
| 0 554 213 | 8/1993 | European Pat. Off. . |
| 0 606 486 | 7/1994 | European Pat. Off. . |
| 0 611 567 | 8/1994 | European Pat. Off. . |
| 56-129035 | 10/1981 | Japan . |
| 4-145131 | 5/1992 | Japan . |
| 4-506931 | 12/1992 | Japan . |
| 6-507884 | 9/1994 | Japan . |
| 227869 | 11/1992 | New Zealand . |
| 01 89/0873 | 10/1989 | South Africa . |
| 1 288 583 | 9/1972 | United Kingdom . |
| WO 84/02838 | 8/1984 | WIPO . |
| WO 90/13780 | 11/1990 | WIPO . |
| WO 91/09629 | 7/1991 | WIPO . |
| WO 91/12823 | 9/1991 | WIPO . |
| WO 91/15244 | 10/1991 | WIPO . |
| WO 92/05806 | 4/1992 | WIPO . |
| WO 92/17212 | 10/1992 | WIPO . |
| WO 92/17213 | 10/1992 | WIPO . |
| WO 92/18164 | 10/1992 | WIPO . |
| WO 93/02712 | 2/1993 | WIPO . |

OTHER PUBLICATIONS

Aldrich, J.E. and Johnston, J.R., "Use of the Spinning Disk Technique to Produce Monodisperse Microspheres of Human Serum Albumin for Labelling with Radioisotopes," *Int. J. Appl. Radiat. Isotopes* 25:15–18 (1974).

Barnhart, J., et al., "Characteristics of Albunex: Air–Filled Albumin Microspheres for Echocardiography Contrast Enhancement," *Invest. Radiol.* 25:s162–s164 (1990).

Basu, S. and Bhattacharya, G., "Some Aspects of the Phenomenon of Coacervation," *Science* 115:544–545 (1952).

Conte, U., et al., "Spray Dried Albumin Microspheres Containing Nicardipine," *Eur. J. Pharm. Biopharm.* 40(4):203–208 (Aug. 1994).

Ellison, J. McK., "Adaptation of the Spinning Top Generator to Provide Aerosols in the Respirable Range," *Ann. Occup. Hyg.* 10 :363–367 (1967).

Feinstein, S.B. et al., "Microbubble Dynamics Visualized in the Intact Capillary Circulation," *J. Am. Coll. Cardiol.* 4(3 ):595–600 (1984).

(List continued on next page.)

*Primary Examiner*—Richard D. Lovering
*Attorney, Agent, or Firm*—Sterne, Kessler, Goldstein and Fox P.L.L.C.

[57] ABSTRACT

Microcapsules are prepared by a process comprising the steps of (i) spray-drying a solution or dispersion of a wall-forming material in order to obtain intermediate microcapsules and (ii) reducing the water-solubility of at least the outside of the intermediate microcapsules.

Suitable wall-forming materials include proteins such as albumin and gelatin.

The microcapsules have walls of 40–500 nm thick and are useful in ultrasonic imaging. The control of median size, size distribution and degree of insolubilisation and cross-linking of the wall-forming material allows novel microsphere preparations to be produced.

11 Claims, 3 Drawing Sheets

U.S. PATENT DOCUMENTS

| | | | |
|---|---|---|---|
| 4,107,288 | 8/1978 | Oppenheim et al. | 424/22 |
| 4,127,622 | 11/1978 | Watanabe et al. | 264/13 |
| 4,173,488 | 11/1979 | Vassiliades et al. | 106/213 |
| 4,276,885 | 7/1981 | Tickner et al. | 128/660 |
| 4,316,391 | 2/1982 | Tickner | 73/861.25 |
| 4,420,442 | 12/1983 | Sands | 264/13 |
| 4,442,843 | 4/1984 | Rasor et al. | 128/660 |
| 4,466,442 | 8/1984 | Hilmann et al. | 128/653 |
| 4,774,958 | 10/1988 | Feinstein | 128/660.01 |
| 4,844,882 | 7/1989 | Widder et al. | 424/9 |
| 4,900,540 | 2/1990 | Ryan et al. | 424/9 |
| 4,957,656 | 9/1990 | Cerny et al. | 252/311 |
| 4,960,351 | 10/1990 | Kendall, Jr. et al. | 425/6 |
| 4,968,562 | 11/1990 | Delgado | 428/402 |
| 4,981,625 | 1/1991 | Rhim et al. | 264/13 |
| 5,069,936 | 12/1991 | Yen | 427/213.33 |
| 5,137,928 | 8/1992 | Erbel et al. | 521/56 |
| 5,190,982 | 3/1993 | Erbel et al. | 521/56 |
| 5,196,183 | 3/1993 | Yudelson et al. | 424/9 |
| 5,205,287 | 4/1993 | Erbel et al. | 128/632 |
| 5,215,680 | 6/1993 | D'Arrigo | 252/307 |
| 5,271,961 | 12/1993 | Mathiowitz et al. | 427/213.31 |
| 5,501,863 | 3/1996 | Rössling et al. | 424/489 |
| 5,518,709 | 5/1996 | Sutton et al. | 424/9.52 |
| 5,543,162 | 8/1996 | Timonen et al. | 426/89 |
| 5,547,656 | 8/1996 | Unger | 424/9.4 |
| 5,567,414 | 10/1996 | Schneider et al. | 424/9.52 |
| 5,643,553 | 7/1997 | Schneider et al. | 424/9.52 |
| 5,674,468 | 10/1997 | Klaveness et al. | 424/9.3 |

OTHER PUBLICATIONS

Galyean, R.D. and Cotterill, O.J., "Chromatography and Electrophoresis of Native and Spray–Dried Egg White," *J. Food Sci.* 44:1345–1349 (1979).

Grinstaff, M.W. and Suslick, K.S., "Air–filled proteinaceous microbubbles: Synthesis of an echo–contrast agent," *Proc. Natl. Acad. Sci. USA* 88: 7708–7710 (1991).

Gupta, P.K. and Hung, C.T., "Albumin microspheres I: physico–chemical characteristics," *J. Microencapsulation* 6(4):427–462 (1989).

Haghpanah, M., et al., abstract presented at British Pharmaceutical Conference, King's College, London (1991).

Heller, J., "Controlled release of biologically active compounds from bioerodible polymers," *Biomaterials* 1:51–57 (1980).

Kawashima, Y. et al., "Preparation of multiple unit hollow microspheres (microballoons) with acrylic resin containing tranilast and their drug release characteristics (in vitro) and floating behavior (in vitro)," *J. Contr. Rel.* 16(3):279–290 (1991).

Kondo, A., *Microcapsule Processing and Technology*, Van Valkenburg, J.W. (Ed.), New York: Marcel Dekker, Inc. pp. 18–20, 61, 68, 70, 90–92, 106–109, 118–119 (1980).

Modler, H.W. and Emmons, D.B., "Calcium as an Adjuvant for Spray–Drying Acid Whey," *J. Dairy Sci.* 61(3):294–299 (1978).

Ophir, J. et al., "Aqueous Solutions as Potential Ultrasonic Contrast Agents," *Ultrasonic Imaging* 1(3):265–279 (1979).

Ophir, J. et al., "Ultrasonic Backscatter from Contrast Producing Collagen Microspheres," *Ultrasonic Imaging* 2:67–77 (1980).

Parkinson, T.L., "Effects of Spray–Drying and Freezing on the Proteins of Liquid Whole Egg," *J. Sci. Fd Agric.* 26:1625–1637 (1975).

Raju, A. et al., "Human Serum Albumin Microspheres for Lung Imaging—Preparation and Evaluation," *Isotopenpraxis* 14(2):57–61 (1978).

Sato, T. et al., "Porous Biodegradable Microspheres for Controlled Drug Delivery. I. Assessment of Processing Conditions and Solvent Removal Techniques," *Pharm. Res.* 5(1):21–30 (1988).

Scheffel, U. et al., "Albumin Microspheres for Study of the Reticuloendothelial System," *J. Nucl. Med.* 13(7):498–503 (1972).

Schlief, R., "Ultrasound contrast agents," *Curr. Opin. Radiol.* 3:198–207 (1991).

Schneider, M. et al., "Polymeric Microballoons as Ultrasound Contrast Agents—Physical and Ultrasonic Properties Compared with Sonicated Albumin," *Investig. Radiol.* 27(2):134–139 (Feb. 1992).

Shapiro, J.R. et al., "Intravenous Contrast Echocardiography With Use of Sonicated Albumin in Humans: Systolic Disappearance of Left Ventricular Contrast After Transpulmonary Transmission," *J. Am. Coll. Cardiol.* 16(7):1603–1607 (1990).

Takenaka, H. et al., "Mechanical Properties, Dissolution Behavior and Stability to Oxidation of L–Ascorbyl–monostearate Microcapsules prepared by a Spray–Drying Polycondensation Technique," *Chem. Pharm. Bull.* 30(6):2189–2195 (1982).

Wheatley, M.A. et al., "Contrast agents for diagnostic ultrasound: development and evaluation of polymer–coated microbubbles," *Biomaterials* 11:713–717 (1990).

Widder, K.J. et al., "Magnetically Responsive Microspheres and Other Carriers for the Biophysical Targeting of Antitumor Agents," *Adv. Pharmacol. Chemother.* 16:213–271 (1979).

Baveja, S. K. et al., "Microencapsulation of soluble pharmaceuticals," *J. Microencasulation* 3(1):33–37 (1986).

Beller, G. A. et al., "Assessment of Regional Myocardial Perfusion by Positron Emission Tomography after Intracoronary Administration of Gallium–68 Labeled Albumin Microspheres," *J. Computer Assisted Tomography* 3(4):447–452 (1979).

Cheng, K. T. et al., "The Production and Evaluation of Contrast–Carrying Liposomes Made with an Automatic High–Pressure System,"0 *Investigative Radiol.* 22(1):47–55 (1987).

Clausen, G. et al., "Distribution of blood flow in the dog kidney. III. Local uptake of 10 $\mu$m and 15 $\mu$m microspheres during renal vasodilation and constriction," *Acta Physiol. Scand.* 113:471–479 (1981).

Cremers, H. F. M. et al., "Albumin–Heparin Microspheres As Carriers for Cytostatic Agents," *J. Controlled Release* 11:167–179 (Jan. 1990).

Davis, S. S. and L. Illum, "Microspheres As Drug Carriers," in: *Drug Carrier Systems*, F. H. D. Roerdink and A. M. Kroon, eds., New York: John Wiley & Sons, Ltd. pp. 131–153 (1989).

Durand–Keklikian, L. and R. E. Partch, "Microencapsulation of Oil Droplets by Aerosol Techniques—I. Metal Oxide Coatings," *J. Aerosol Sci.* 19(4):511–521 (1988).

Kwok, K. K. et al., "Production of 5–15 $\mu$m Diameter Alginate–Polylysine Microcapsules by an Air–Atomization Technique," *Pharm. Res.* 8(3):341–344 (Mar. 1991).

Levy, M.–C. and M.–C. Andry, "Mixed—walled microcapsules made of cross–linked proteins and polysaccharides: preparation and properties," *J. Microencapsulation* 8(3):335–347 (Sep. 1991).

McArdle, C. S. et al., "Cytotoxic loaded albumin microspheres: a novel approach to regional chemotherapy," *Br. J. Surg.* 75:132–134 (1988).

Pande, S. et al., "Preparation, chacterization and performance evaluation of neomycin–HSA microspheres," *J. Microencapsulation* 7(2):155–165 (Jun. 1990).

Porter, C. J. H., "The polyoxyethylene/polyoxypropylene block co–polymer Poloxamer–407 selectively redirects intravenously injected microspheres to sinusoidal endothelial cells of rabbit bone marrow," *FEBS Lett.* 305(1):62–66 (Jun. 1992).

Rosenberg, M. et al., "Factors Affecting Retention in Spray–Drying Microencapsulation of Volatile Materials," *J. Agric. Food Chem.* 38(5):1288–1294 (May 1990).

Takenaka, H. et al., "Preparation of Enteric–Coated Microcapsules for Tableting by Spray–Drying Technique and In Vitro Simulation of Drug Release from the Tablet in GI Tract," *J. Pharm. Sci.* 69(1):1388–1392 (1980).

Violante, M. R. et al., "Biodistribution of a Paraticulate Hepatolienographic CT Contrast Agent: A Study of Iodopamide Ethyl Ester in the Rat," *Investigative Radiol.* 16(1):40–45 (1981).

White, C. et al., "Biodistribution and Clearance of Contrast–Carrying MREV Liposomes," *Investigative Radiol.* 25(10):1125–1129 (Oct. 1990).

Wilkins, D. J. and P. A. Myers, "Studies on the Relationship Between the Electrophoretic Properties of Colloids and Their Blood Clearance and Organ Distribution in the Rat," pp. 568–576 Br. J. Exp. Patho. (Dec. 1966).

Zhang, D. et al., "Histochemical studies on the mechanism of macromolecule leakage across the glomerular capillary wall," *Histochem.* 96:115–121 (Jun. 1991).

PREPARATION OF DIAGNOSTIC AGENTS

This application is a continuation of application Ser. No. 07/956,875, filed Mar. 11, 1993, (now U.S. Pat. No. 5,518, 709), which is a 371 of PCT/GB92/00643 filed Apr. 10, 1992, which claims priority based on GB91/07628, filed Apr. 10, 1991.

The present invention relates to the preparation of diagnostic agents comprising hollow proteinaceous microcapsules used to enhance ultrasound imaging.

The fact that air bubbles in the body can be used for echocardiography has been known for some time. Bubble-containing liquids can be injected into the bloodstream for this purpose (see Ophir et al (1980) "Ultrasonic Imaging" 2, 67–77, who stabilised bubbles in a collagen membrane, U.S. Pat. No. 4,446,442 (Schering) and EP-A-131 540 (Schering)) and EP-A-224934 and EP-A-324938 disclose the use of bubbles prepared by sonicating an albumin solution. However, the size distribution of the bubbles is apparently uncontrollable and the bubbles disappear when subjected to pressure experienced in the left ventricle (Shapiro et al (1990) *J. Am. Coll. Cardiology*, 16(7), 1603–1607).

EP-A-52575 discloses, for the same purpose, solid particles which have gas entrained in them, the gas being released from the particles in the bloodstream.

EP 458 745 (Sintetica) discloses a process of preparing air- or gas-filled microballoons by interfacial polymerisation of synthetic polymers such as polylactides and polyglycolides. WO 91/12823 (Delta) discloses a similar process using albumin. Wheatley et al (1990) *Biomaterials* 11, 713–717 discloses ionotropic gelation of alginate to form microbubbles of over 30 μm diameter. Wo 91/09629 discloses liposomes for use as ultrasound contrast agents.

We have now found that a process of atomising a solution of microcapsule-forming agent and then insolubilising the microcapsules which are formed leads to an improved product. Przyborowski et al (1982 *Eur. J. Nucl. Med.* 7, 71–72) disclosed the preparation of human serum albumin (HSA) microspheres by spray-drying for radiolabelling and subsequent use in scintigraphic imaging of the lung. The microspheres were not said to be hollow and, in our repetition of the work, only solid microspheres are produced. Unless the particles are hollow, they are unsuitable for echocardiography. Furthermore, the microspheres were prepared in a one step process which we have found to be unsuitable for preparing microcapsules suitable for echocardiography; it was necessary in the prior process to remove undenatured albumin from the microspheres (which is not necessary in our process); and a wide size range of microspheres was apparently obtained, as a further sieving step was necessary. Hence, not only was the Przyborowski et al process not an obvious one to choose for the preparation of microcapsules useful in ultrasonic imaging but the particles produced were unsuitable for that purpose. We have devised a considerable improvement over that prior process.

The Przyborowski et al article refers to two earlier disclosures of methods of obtaining albumin particles for lung scintigraphy. Aldrich & Johnston (1974) *Int. J. Appl. Rad. Isot.* 25, 15–18 disclosed the use of a spinning disc to generate 3–70 μm diameter particles which are then denatured in hot oil. The oil is removed and the particles labelled with radioisotopes. Raju et al (1978) *Isotopenpraxis* 14(2), 57–61 used the same spinning disc technique but denatured the albumin by simply heating the particles. In neither case were hollow microcapsules mentioned and the particles prepared were not suitable for echocardiography.

One aspect of the present invention provides a process comprising a first step of atomising a solution or dispersion of a wall-forming material in order to obtain microcapsules.

Preferably, the product obtained thereby is subjected to a second step of reducing the water-solubility of at least the outside of the said microcapsules.

The said two steps may be carried out as a single process or the intermediate product of the first step may be collected and separately treated in the second step. These two possibilities are referred to hereinafter as the one step and two step processes.

The wall-forming material and process conditions should be so chosen that the product is sufficiently non-toxic and non-immunogenic in the conditions of use, which will clearly depend on the dose administered and duration of treatment. The wall-forming material may be a starch derivative, a synthetic polymer such as tert-butyloxycarbonylmethyl polyglutamate (U.S. Pat. No. 4,888,398) or a polysaccharide such as polydextrose.

Generally, the wall-forming material can be selected from most hydrophilic, biodegradable physiologically compatible polymers. Among such polymers one can cite polysaccharides of low water solubility, polylactides and polyglycolides and their copolymers, copolymers of lactides and lactones such as ε-caprolactone, δ-valerolactone, polypeptides, and proteins such as gelatin, collagen, globulins and albumins. Other suitable polymers include poly-(ortho)esters (see for instance U.S. Pat. Nos. 4,093,709; 4,131,648; 4,138,344; 4,180,646; polylactic and polyglycolic acid and their copolymers, for instance DEXON (see J. Heller (1980) *Biomaterials* 1, 51; poly(DL-lactide-co-δ-caprolactone), poly(DL-lactide-co-δ-valerolactone), poly (DL-lactide-co-g-butyrolactone), polyalkylcyanoacrylates; polyamides, polyhydroxybutyrate; polydioxanone; poly-β-aminoketones (*Polymer* 23 (1982), 1693); polyphosphazenes (*Science* 193 (1976), 1214); and polyanhydrides. References on biodegradable polymers can be found in R. Langer et al (1983) *Macromol. Chem. Phys.* C23, 61–125. Polyamino-acids such as polyglutamic and polyaspartic acids can also be used as well as their derivatives, ie partial esters with lower alcohols or glycols. One useful example of such polymers is poly-(t,butyl-glutamate). Copolymers with other amino-acids such as methionine, leucine, valine, proline, glycine, alamine, etc are also possible. Recently some novel derivatives of polyglutamic and polyaspartic acid with controlled biodegradability have been reported (see WO 87/03891; U.S. Pat. No. 4,888,398 and EP 130 935 incorporated here by reference). These polymers (and copolymers with other amino-acids) have formulae of the following type:

where X designates the side chain of an amino-acid residue and A is a group of formula —(CH$_2$)$_n$COOR$^1$R$^2$OCOR(II), with R$^1$ and R$^2$ being H or lower alkyls, and R being alkyl or aryl; or R and R$^1$ are connected together by a substituted or unsubstituted linking member to provide 5- or 6-membered rings.

A can also represent groups of formulae:

and

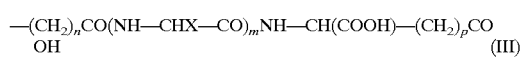

and corresponding anhydrides. In all these formulae n, m and p are lower integers (not exceeding 5) and x and y are also integers selected for having molecular weights not below 5000.

The aforementioned polymers are suitable for making the microspheres according to the invention and, depending on the nature of substituents R, $R^1$, $R^2$ and X, the properties of the wall can be controlled, for instance, strength, elasticity and biodegradability. For instance X can be methyl (alanine), isopropyl (valine), isobutyl (leucine and isoleucine) or benzyl (phenylalanine).

Preferably, the wall-forming material is proteinaceous. For example, it may be collagen, gelatin or (serum) albumin, in each case preferably of human origin (ie derived from humans or corresponding in structure to the human protein). Most preferably, it is human serum albumin (HA) derived from blood donations or, ideally, from the fermentation of microorganisms (including cell lines) which have been transformed or transfected to express HA.

Techniques for expressing HA (which term includes analogues and fragments of human albumin, for example those of EP-A-322094, and polymers of monomeric albumin) are disclosed in, for example, EP-A-201239 and EP-A-286424. All references are included herein by reference. "Analogues and fragments" of HA include all polypeptides (i) which are capable of forming a microcapsule in the process of the invention and (ii) of which a continuous region of at least 50% (preferably at least 75%, 80%, 90% or 95%) of the amino acid sequence is at least 80% homologous (preferably at least 90%, 95% or 99% homologous) with a continuous region of at least 50% (preferably 75%, 80%, 90% or 95%) of human albumin. HA which is produced by recombinant DNA techniques is particularly preferred. Thus, the HA may be produced by expressing an HA-encoding nucleotide sequence in yeast or in another microorganism and purifying the product, as is known in the art. Such material lacks the fatty acids associated with serum-derived material. Preferably, the HA is substantially free of fatty acids; ie it contains less than 1% of the fatty acid level of serum-derived material. Preferably, fatty acid is undetectable in the HA.

In the following description of preferred embodiments, the term "protein" is used since this is what we prefer but it is to be understood that other biocompatible wall-forming materials can be used, as discussed above.

The protein solution or dispersion is preferably 0.1 to 50% w/v, more preferably about 5.0–25.0% protein, particularly when the protein is albumin. About 20% is optimal. Mixtures of wall-forming materials may be used, in which case the percentages in the last two sentences refer to the total content of wall-forming material.

The preparation to be sprayed may contain substances other than the wall-forming material and solvent or carrier liquid. Thus, the aqueous phase may contain 1–20% by weight of water-soluble hydrophilic compounds like sugars and polymers as stabilizers, eg polyvinyl alcohol (PVA), polyvinyl pyrrolidone (PVP), polyethylene glycol (PEG), gelatin, polyglutamic acid and polysaccharides such as starch, dextran, agar, xanthan and the like. Similar aqueous phases can be used as the carrier liquid in which the final microsphere product is suspended before use. Emulsifiers may be used (0.1–5% by weight) including most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose.

Additives can be incorporated into the wall of the microspheres to modify the physical properties such as dispersibility, elasticity and water permeability.

Among the useful additives, one may cite compounds which can "hydrophobize" the wall in order to decrease water permeability, such as fats, waxes and high molecular-weight hydrocarbons. Additives which improve dispersibility of the microspheres in the injectable liquid-carrier are amphipathic compounds like the phospholipids; they also increase water permeability and rate of biodegradability.

Additives which increase wall elasticity are the plasticizers like isopropyl myristate and the like. Also, very useful additives are constituted by polymers akin to that of the wall itself but with relatively low molecular weight. For instance when using copolymers of polylactic/polyglycolic type as the wall-forming material, the properties of the wall can be modified advantageously (enhanced softness and biodegradability) by incorporating, as additives, low molecular weight (1000 to 15,000 Dalton) polyglycolides or polylactides. Also polyethylene glycol of moderate to low Mw (eg PEG 2000) is a useful softening additive.

The quantity of additives to be incorporated in the wall is extremely variable and depends on the needs. In some cases no additive is used at all; in other cases amounts of additives which may reach about 20% by weight of the wall are possible.

The protein solution or dispersion (preferably solution), referred to hereinafter as the "protein preparation", is atomised and spray-dried by any suitable technique which results in discrete microcapsules of 1.00–50.0 $\mu$m diameter. These figures refer to at least 90% of the population of microcapsules, the diameter being measured with a Coulter Master Sizer II. The term "microcapsules" means hollow particles enclosing a space, which space is filled with a gas or vapour but not with any solid materials. Honeycombed particles resembling the confectionery sold in the UK as "Maltesers" (Regd TM) are not formed. It is not necessary for the space to be totally enclosed (although this is preferred) and it is not necessary for the microcapsules to be precisely spherical, although they are generally spherical. If the microcapsules are not spherical, then the diameters referred to above relate to the diameter of a corresponding spherical microcapsule having the same mass and enclosing the same volume of hollow space as the non-spherical microcapsule.

The atomising comprises forming an aerosol of the protein preparation by, for example, forcing the preparation through at least one orifice under pressure into, or by using a centrifugal atomizer in a chamber of warm air or other inert gas. The chamber should be big enough for the largest ejected drops not to strike the walls before drying. The gas or vapour in the chamber is clean (ie preferably sterile and pyrogen-free) and non-toxic when administered into the bloodstream in the amounts concomitant with administration of the microcapsules in echocardiography. The rate of evaporation of the liquid from the protein preparation should be sufficiently high to form hollow microcapsules but not so high as to burst the microcapsules. The rate of evaporation may be controlled by varying the gas flow rate, concentration of protein in the protein preparation, nature of liquid carrier, feed rate of the solution and, most importantly, the temperature of the gas encountered by the aerosol. With an albumin concentration of 15–25% in water, an inlet gas temperature of at least about 100° C., preferably at least 110° C., is generally sufficient to ensure hollowness and the temperature may be as high as 250° C. without the capsules bursting. About 180–240° C., preferably about 210–230° C. and most preferably about 220° C., is optimal, at least for albumin. The temperature may, in the one step version of the process of the invention, be sufficient to insolubilise at least part (usually the outside) of the wall-forming material and frequently substantially all of the wall-forming material. Since the temperature of the gas encountered by the aerosol will depend also on the rate at which the aerosol is delivered and on the liquid content of the protein preparation, the outlet temperature may be monitored to ensure an adequate temperature in the chamber. An outlet temperature of 40–150° C. has been found to be suitable. Apart from this factor, however, controlling the flow rate has not been found to be as useful as controlling the other parameters.

In the two step process, the intermediate microcapsules comprise typically 96–98% monomeric HA and have a limited in vivo life time for ultrasound imaging. They may, however, be used for ultrasound imaging, or they may be stored and transported before the second step of the two step process is carried out. They therefore form a further aspect of the invention.

In the second step of the process, the intermediate microcapsules prepared in the first step are fixed and rendered less water-soluble so that they persist for longer whilst not being so insoluble and inert that they are not biodegradable. This step also strengthens the microcapsules so that they are better able to withstand the rigours of administration, vascular shear and ventricular pressure. If the microcapsules burst, they become less echogenic. Schneider et al (1992) *Invest. Radiol.* 27, 134–139 showed that prior art sonicated albumin microbubbles do not have this strength and rapidly lose their echogenicity when subjected to pressures typical of the left ventricle. The second step of the process may employ heat (for example microwave heat, radiant heat or hot air, for example in a conventional oven), ionising irradiation (with, for example, a 10.0–100.0 kGy dose of gamma rays) or chemical cross-linking using, for example, formaldehyde, glutaraldehyde, ethylene oxide or other agents for cross-linking proteins and is carried out on the substantially dry intermediate microcapsules formed in the first step, or on a suspension of such microcapsules in a liquid in which the microcapsules are insoluble, for example a suitable solvent. In the one step version of the process, a cross-linking agent such as glutaraldehyde may be sprayed into the spray-drying chamber or may be introduced into the protein preparation just upstream of the spraying means. Alternatively, the temperature in the chamber may be high enough to insolubilise the microcapsules.

The final product, measured in the same way as the intermediate microcapsules, may, if one wishes, consist of microcapsules having a diameter of 0.05 to 50.0 $\mu$m, but ranges of 0.1 to 20.0 $\mu$m and especially 1.0 to 8.0 $\mu$m are obtainable with the process of the invention and are preferred for echocardiography. We have found that a range of about 0.5 to 3.0 $\mu$m may be especially suitable for the production of a low contrast image and for use in colour Doppler imaging, whereas a range of about 4.0 to 6.0 $\mu$m may be better for the production of sharp images. One needs to take into account the fact that the second step may alter the size of the microcapsules in determining the size produced in the first step.

It has been found that the process of the invention can be controlled in order to obtain microspheres with desired characteristics. Thus, the pressure at which the protein solution is supplied to the spray nozzle may be varied, for example from $1.0–10.0 \times 10^5$ Pa, preferably $2.0–6.0 \times 10^5$ Pa and most preferably about $5 \times 10^5$ Pa. Other parameters may be varied as disclosed above and below. In this way, novel microspheres may be obtained.

A further aspect of the invention provides hollow microspheres in which more than 30%, preferably more than 40%, 50%, or 60%, of the microspheres have a diameter within a 2 $\mu$m range and at least 90%, preferably at least 95% or 99%, have a diameter within the range 1.0–8.0 $\mu$m.

Thus, the interquartile range may be 2 $\mu$m, with a median diameter of 3.5, 4.0, 4.5, 5.0, 5.5, 6.0 or 6.5 $\mu$m.

Thus, at least 30%, 40%, 50% or 60% of the microspheres may have diameters within the range 1.5–3.5 $\mu$m, 2.0–4.0 $\mu$m, 3.0–5.0 $\mu$m, 4.0–6.0 $\mu$m, 5.0–7.0 $\mu$m or 6.0–8.0 $\mu$m. Preferably a said percentage of the microspheres have diameters within a 1.0 $\mu$m range, such as 1.5–2.5 $\mu$m, 2.0–3.0 $\mu$m, 3.0–4.0 $\mu$m, 4.0–5.0 $\mu$m, 5.0–6.0 $\mu$m, 6.0–7.0 $\mu$m or 7.0–8.0 $\mu$m.

A further aspect of the invention provides hollow microspheres with proteinaceous walls in which at least 90%, preferably at least 95% or 99%, of the microspheres have a diameter in the range 1.0–8.0 $\mu$m; at least 90%, preferably at least 95% or 99%, of the microspheres have a wall thickness of 40–500 nm, preferably 100–500 nm; and at least 50% of the protein in the walls of the microspheres is cross-linked. Preferably, at least 75%, 90%, 95%, 98.0%, 98.5% or 99% of the protein is sufficiently cross-linked to be resistant to extraction with a 1% HCl solution for 2 minutes. Extracted protein is detected using the Coomassie Blue protein assay, Bradford. The degree of cross-linking is controlled by varying the heating, irradiation or chemical treatment of the protein. During the cross-linking process, protein monomer is cross-linked and quickly becomes unavailable in a simple dissolution process, as detected by gel permeation HPLC or gel electrophoresis, as is shown in Example 8 below. Continued treatment leads to further cross-linking of already cross-linked material such that it becomes unavailable in the HCl extraction described above. During heating at 175° C., rHA microspheres in accordance with the invention lose about 99% of HCl-extractable protein over the course of 20 minutes, whereas, at 150° C., 20 minutes' heating removes only about 5% HCl -extractable protein, 30 mins removes 47.5%, 40 mins 83%, 60 mins 93%, 80 mins 97% and 100 mins removes 97.8% of the HCl-extractable protein. To achieve good levels of cross-linking therefore, the microspheres may be heated at 175° C. for at least 17–20 mins, at 150° C. for at least 80 mins and at other temperatures for correspondingly longer or shorter times.

A further aspect of the invention provides hollow microspheres predominantly of 1.0–10.0 $\mu$m in diameter, at least 10% of the microspheres, when suspended in water, being capable of surviving a 0.25 s application of a pressure of $2.66 \times 10^4$ Pa without bursting, collapsing or filling with water. The transient maximum pressure in the human left ventricle is about 200 mmHg ($2.66 \times 10^4$ Pa). Preferably 50%, 75%, 90% or 100% survive the said 0.25 s application of $2.66 \times 10^4$ Pa when tested as above, ie remain echogenic. In vivo, preferably the same percentages will remain echogenic during one passage through both ventricles of the heart.

The injectable microspheres of the present invention can be stored dry in the presence or in the absence of additives to improve conservation and prevent coalescence. As additives, one may select from 0.1 to 25% by weight of water-soluble physiologically acceptable compounds such as mannitol, galactose, lactose or sucrose or hydrophilic polymers like dextran, xanthan, agar, starch, PVP, polyglutamic acid, polyvinylalcohol (PVA) and gelatin. The useful life-time of the microspheres in the injectable liquid carrier phase, ie the period during which useful echographic signals are observed, can be controlled to last from a few minutes to several months depending on the needs; this can be done by controlling the porosity, solubility or degree of cross-linking of the wall. These parameters can be controlled by properly selecting the wall-forming materials and additives and by adjusting the evaporation rate and temperature in the spray-drying chamber.

In order to minimise any agglomeration of the microcapsules, the microcapsules can be milled with a suitable inert excipient using a Fritsch centrifugal pin mill equipped with a 0.5 mm screen, or a Glen Creston air impact jet mill. Suitable excipients are finely milled powders which are inert and suitable for intravenous use, such as lactose, glucose, mannitol, sorbitol, galactose, maltose or sodium chloride. Once milled, the microcapsules/excipient mixture can be suspended in aqueous medium to facilitate removal of non-functional/defective microcapsules. Upon reconstitution in the aqueous phase, it is desirable to include a trace amount of surfactant to prevent agglomeration. Anionic, cationic and non-ionic surfactants suitable for this purpose include poloxamers, sorbitan esters, polysorbates and lecithin.

The microcapsule suspension may then be allowed to float, or may be centrifuged to sediment any defective particles which have surface defects which would, in use, cause them to fill with liquid and be no longer echogenic.

The microcapsule suspension may then be remixed to ensure even particle distribution, washed and reconstituted in a buffer suitable for intravenous injection such as 0.15M NaCl 0.01 mM Tris pH 7.0. The suspension may be aliquoted for freeze drying and subsequent sterilisation by, for example, gamma irradiation, dry heating or ethylene oxide.

An alternative method for deagglomeration of the insolubilised or fixed microcapsules is to suspend them directly in an aqueous medium containing a surfactant chosen from poloxamers, sorbitan esters, polysorbates and lecithin. Deagglomeration may then be achieved using a suitable homogeniser.

The microcapsule suspension may then be allowed to float or may be centrifuged to sediment the defective particles, as above, and further treated as above.

Although the microspheres of this invention can be marketed in the dry state, more particularly when they are designed with a limited life time after injection, it may be desirable to also sell ready-made preparations, ie suspensions of microspheres in an aqueous liquid carrier ready for injection.

The product is generally, however, supplied and stored as a dry powder and is suspended in a suitable sterile, non-pyrogenic liquid just before administration. The suspension is generally administered by injection of about 1.0–10.0 ml into a suitable vein such as the cubital vein or other bloodvessel. A microcapsule concentration of about $1.0 \times 10^5$ to $1.0 \times 10^{12}$ particles/ml is suitable, preferably about $5.0 \times 10^5$ to $5.0 \times 10^9$.

Although ultrasonic imaging is applicable to various animal and human body organ systems, one of its main applications is in obtaining images of myocardial tissue and perfusion or blood flow patterns.

The techniques use ultrasonic scanning equipment consisting of a scanner and imaging apparatus. The equipment produces visual images of a predetermined area, in this case the heart region of a human body. Typically, the transducer is placed directly on the skin over the area to be imaged. The scanner houses various electronic components including ultrasonic transducers. The transducer produces ultrasonic waves which perform a sector scan of the heart region. The ultrasonic waves are reflected by the various portions of the heart region and are received by the receiving transducer and processed in accordance with pulse-echo methods known in the art. After processing, signals are sent to the imaging apparatus (also well known in the art) for viewing.

In the method of the present invention, after the patient is "prepped" and the scanner is in place, the microcapsule suspension is injected, for example through an arm vein. The contrast agent flows through the vein to the right venous side of the heart, through the main pulmonary artery leading to the lungs, across the lungs, through the capillaries, into the pulmonary vein and finally into the left atrium and the left ventricular cavity of the heart.

With the microcapsules of this invention, observations and diagnoses can be made with respect to the amount of time required for the blood to pass through the lungs, blood flow patterns, the size of the left atrium, the competence of the mitral valve (which separates the left atrium and left ventricle), chamber dimensions in the left ventricular cavity and wall motion abnormalities. Upon ejection of the contrast agent from the left ventricle, the competence of the aortic valve also may be analyzed, as well as the ejection fraction or percentage of volume ejected from the left ventricle. Finally, the contrast patterns in the tissue will indicate which areas, if any, are not being adequately perfused.

In summary, such a pattern of images will help diagnose unusual blood flow characteristics within the heart, valvular competence, chamber sizes and wall motion, and will provide a potential indicator of myocardial perfusion.

The microcapsules may permit left heart imaging from intravenous injections. The albumin microcapsules, when injected into a peripheral vein, may be capable of transpulmonary passage. This results in echocardiographic opacification of the left ventricle (LV) cavity as well as myocardial tissue.

Besides the scanner briefly described above, there exist other ultrasonic scanners, examples of which are disclosed in U.S. Pat. Nos. 4,134,554 and 4,315,435, the disclosures of which are herein incorporated by reference. Basically, these patents relate to various techniques including dynamic cross-sectional echography (DCE) for producing sequential two-dimensional images of cross-sectional slices of animal or human anatomy by means of ultrasound energy at a frame rate sufficient to enable dynamic visualisation of moving organs. Types of apparatus utilised in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualisation of tissue and major blood vessels of the heart.

The microcapsules may be used for imaging a wide variety of areas, even when injected at a peripheral venous site. Those areas include (without limitation): (1) the venous drainage system to the heart; (2) the myocardial tissue and perfusion characteristics during an exercise treadmill test or the like; and (3) myocardial tissue after an oral ingestion or intravenous injection of drugs designed to increase blood flow to the tissue. Additionally, the microcapsules may be useful in delineating changes in the myocardial tissue perfusion due to interventions such as (1) coronary artery vein grafting; (2) coronary artery angioplasty (balloon dilation of a narrowed artery); (3) use of thrombolytic agents (such as streptokinase) to dissolve clots in coronary arteries; or (4) perfusion defects or changes due to a recent heart attack.

Furthermore, at the time of -a coronary angiogram (or a digital subtraction angiogram) an injection of the microcapsules may provide data with respect to tissue perfusion characteristics that would augment and complement the data obtained from the angiogram procedure, which identifies only the anatomy of the blood vessels.

Through the use of the microcapsules of the present invention, other non-cardiac organ systems including the liver, spleen and kidney that are presently imaged by ultrasonic techniques may be suitable for enhancement of such currently obtainable images, and/or the generation of new images showing perfusion and flow characteristics that had not previously been susceptible to imaging using prior art ultrasonic imaging techniques.

BRIEF DESCRIPTION OF THE FIGURES

Preferred aspects of the present invention will now be described by way of example and with reference to FIG. 1, which is a partly cut away perspective view from the front and one side of suitable spray-drying apparatus for the first stage of the process of the invention, FIG. 2, which is a graph showing how the degree of fixation of the microsphere walls (in this case albumin) may be controlled by varying the temperature and the heating time in the second step of the process, and FIG. 3, which is a graph showing how the pressure resistivity of the microspheres may be varied by altering the length of the heating time in the second step of the process.

EXAMPLE 1

Figure 1:
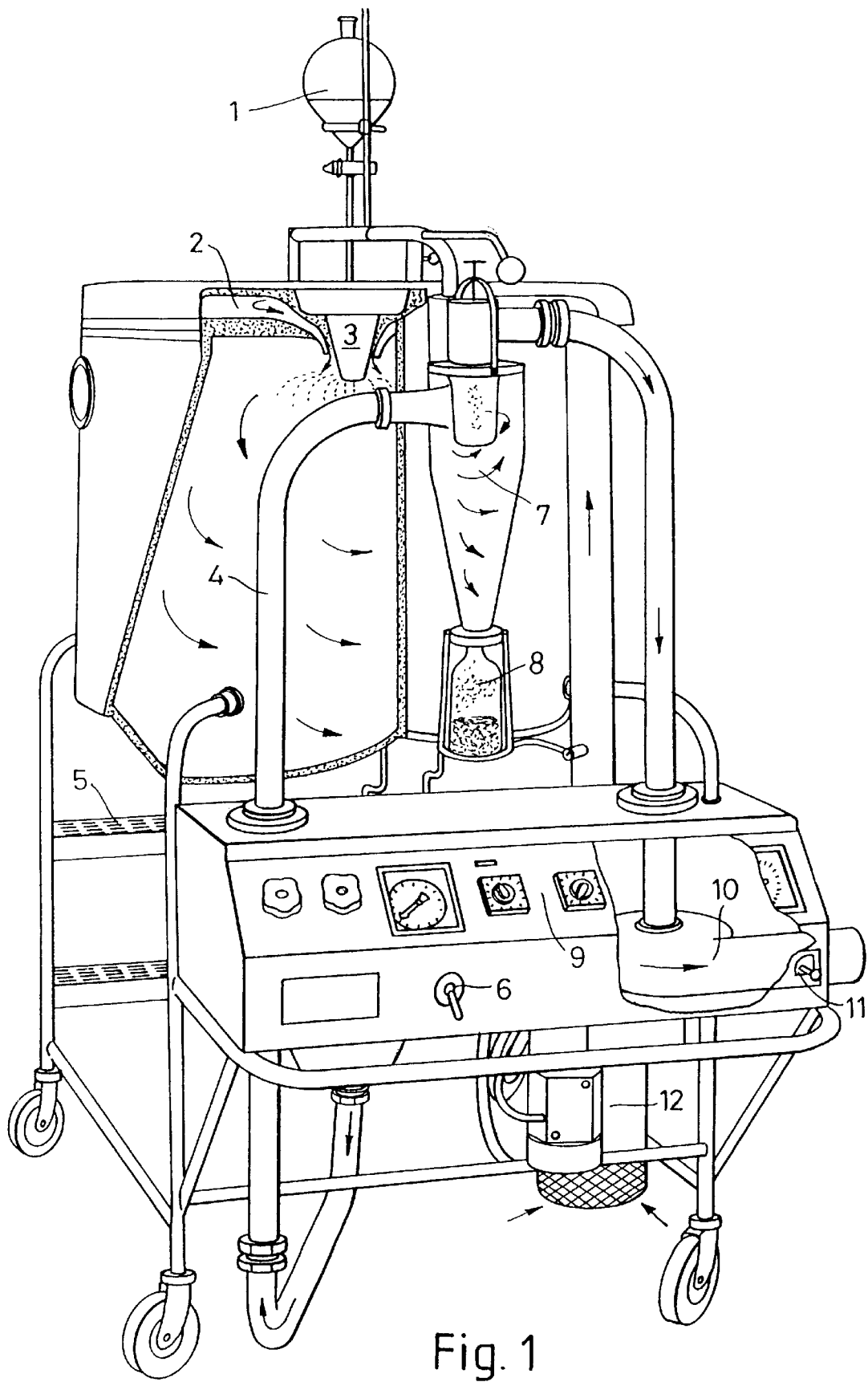

A suitable spray dryer (FIG. 1) is available from A/S Niro Atomizer, Soeborg, Denmark under the trade designation "Mobile Minor". Details of its construction are given immediately before the claims herein. It comprises a centrifugal atomizer (Type M-02/B Minor), driven by an air turbine at an air pressure of min 4 bar and up to max 6 bar. At 6 bar an atomizer wheel speed of approx 33,000 rpm is reached. Turning on and off the compressed air to the atomizer is done by means of a valve placed in the instrument panel. The maximum consumption of compressed air to the atomizer is 17 Nm$^3$/h at a pressure of 6 bar. All parts coming into contact with the liquid feed and powder are made of stainless steel AISI 316, except for the pump feed tube and the atomizer wheel, which is made of stainless steel AISI 329, made to resist high centrifugal force.

The drying chamber has an inside made of stainless steel AISI 316, well insulated with Rockwool, and covered outside with a mild steel sheeting. The drying chamber is provided with a side light and observation pane for inspection during the operation. The roof of the drying chamber is made inside of stainless steel AISI 316 and outside of stainless steel AISI 304.

An air disperser made of stainless steel AISI 304 is used for distribution of the air in the drying chamber in order to achieve the best possible drying effect. An air duct, made of stainless steel AISI 316, provides lateral transportation of the exhaust air and the powder to the cyclone, which is made of stainless steel AISI 316 and designed to separate the powder and air.

A closing valve of the butterfly valve type, also made of stainless steel AISI 316 and having a gasket of silicone rubber, is used for powder discharge under the cyclone into a powder collecting glass jar tightly placed under the cyclone by means of a spring device.

A fan made of silumin, complete with 3-phase squirrel-cage motor, 0.25 kw, and V-belt drive with belt-guard, draws air and powder through the drying chamber and cyclone.

An air heater heats the drying air by means of electricity (total consumption 7.5 kWh/h, infinitely variable) and can give inlet air temperatures of up to about 350° C., although this is generally too high for preparing the microcapsules of the invention.

Equipment for two-fluid nozzle atomization may be added, which is made of stainless steel AISI 316, consisting of entrance pipe with nozzle holder and nozzle, to be placed in the ceiling of the drying chamber. The equipment includes an oil/water separator, reduction valve and pressure gauge for compressed air to the two-fluid nozzle. Consumption of compressed air: 8–15 kg/h at a pressure of 0.5–2.0 bar (0.5–2.0×10$^5$ Pa).

A suitable feed pump for transport of wall-forming preparation feed to the atomizer device is a peristaltic pump. The pump is provided with a motor (1×220 V, 50 Hz, 0.18 kW) and a continuously variable gear for manual adjustment. A feed pipe made of silicone hose leads from a feed tank (local supply) through the feed pump to the atomization device.

An absolute air filter, consisting of prefilter, filter body in stainless steel and absolute air filter, is used for the treatment of the ingoing drying air to render it completely clean.

A 20% solution of sterile, pyrogen-free rHA in pyrogen-free water (suitable for injection) was pumped to the nozzle of a two fluid nozzle atomiser mounted in the commercial spray drying unit described above. The peristaltic pump speed was maintained at a rate of approximately 10 ml/minute such that with an inlet air temperature of 220° C. the outlet air temperature was maintained at 95° C.

Compressed air was supplied to the two fluid atomising ozzle at 2.0–6.0 Bar (2.0–6.0×10$^5$Pa). In this range microcapsules with a mean size of 4.25–6.2 μm are obtained.

Typically an increase in mean particle size (by reduced atomisation pressure) led to an increase in the amount of microcapsules over 10 μm in size (see Table 1).

TABLE 1

EFFECTS OF ATOMISATION PRESSURE ON FREQUENCY OF MICROCAPSULES OVER 10 μM IN DIAMETER

| Atomisation Pressure (×10$^5$ Pa) | % Frequency over 10 μm |
|---|---|
| 6.0 | 0.8 |
| 5.0 | 0.3 |
| 3.5 | 6.6 |
| 2.5 | 8.6 |
| 2.0 | 13.1 |

In the second step of the process, 5 g of microcapsules were heated in a glass beaker using a Gallenkamp fan oven. A temperature of 175° C. for 1 hour was sufficient to yield microcapsules with 100% fixation as determined by HPLC.

Figure 2:
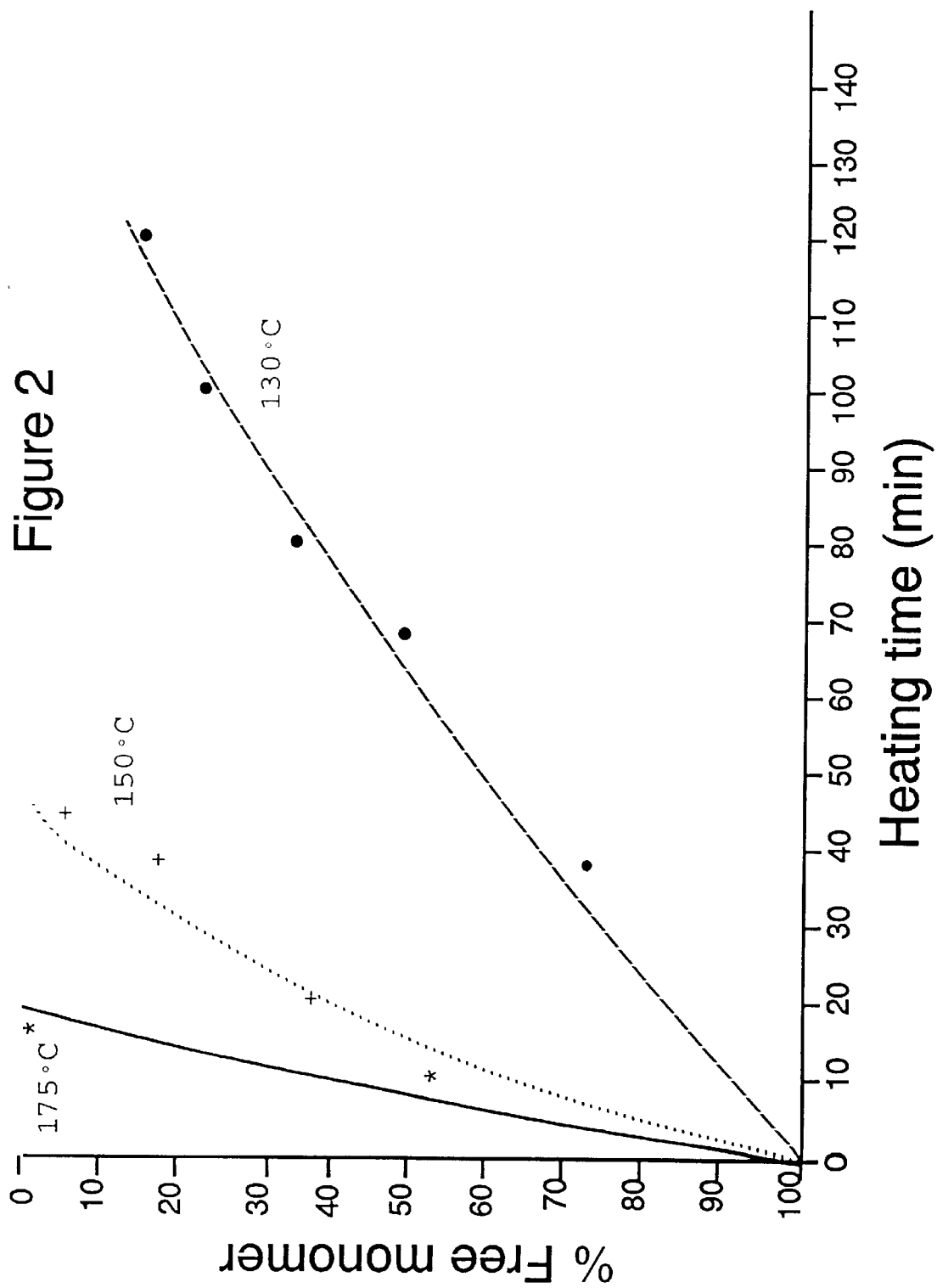

The effect of this heat fixation was to increase the in vitro echogenic half life from a few seconds to in excess of 30 minutes. By altering the temperature and length of incubation it is possible to vary the degree of fixation between about 5% and 100%. Examples of heat fixation profiles of varying temperatures are shown in FIG. 2.

Following heat fixation, the microcapsules were deagglomerated and dispersed into water in one of two ways. Method 1 involved first mixing the heat fixed spheres with an equal weight of finely milled lactose (mean diameter 5 μm). The mixture was then passed through a Fritsch centrifugal mill with a 0.5 mm screen and 12 tooth rotor. The milled spheres were collected and passed through the mill a second time to ensure complete mixing had occurred. The milled powder was then resuspended in water containing 1 mg.ml$^{-1}$ Pluronic F68. Typically 10 g of microcapsules and lactose was added to 100 ml of water and Pluronic F68. Method 2 for deagglomeration involves adding 5 g of the heat-fixed microcapsules to 100 ml of water containing 100 mg of Pluronic F68. The microcapsules were dispersed using a Silverson homogeniser (model L4R with a 2.54 cm tubular homogenising probe and a high shear screen) and homogenising for 60 seconds.

The resuspended spheres were separated into intact (gas containing) and broken spheres using a flotation technique. The gas-containing spheres were seen to float to the surface over a 1 hour period and were decanted from the sinking fraction which does not contain the gas required.

The separation process can be accelerated by centrifugation. A 30 second centrifugation at 5000×g is sufficient to separate the two fractions.

Following separation the intact microcapsules were freeze-dried in the presence of lactose and Pluronic F68. Optimal conditions for freeze drying involved resuspending 30 mg of microcapsules in 5 ml of water containing 50 mg of lactose and 5 mg of Pluronic F68. The freeze-dried microcapsules can be redispersed in a liquid (eg water, saline) to give a monodisperse distribution.

EXAMPLE 2

The process of Example 1 was repeated but with the following differences in the first step: a centrifugal atomiser was used instead of a two fluid nozzle; the inlet temperature was 150° C. (with the outlet air temperature still being sustained at 105° C.); and compressed air was supplied to the nozzle at 1.0–6.0×10$^5$ Pa. The wheel rotated at 20–40,000 rpm and delivered droplets, and subsequently microcapsules, with a number mean diameter in the 1.0–8.0 μm range.

EXAMPLE 3

In the second step of the process of Example 1 or 2 was varied as follows. A small aliquot of the microcapsules (0.5 g) was heated in a microwave oven such that it received 300–350 watt hours of microwave heat at 2500 mHz. This yielded microcapsules in which 90–95% of the monomeric rHA was insoluble (as determined by gel permeation chlomatography) and as a result of this heat fixation their in vitro echogenic half-life increased from a few seconds to in excess of 30 minutes.

EXAMPLE 4

In the second step of the process of Example 1 or 2 was varied as follows. A small aliquot of the microcapsules (0.5 g) was sealed under argon in a glass vial. The vial was cooled to 4° C. and then irradiated with a $^{60}Co$ gamma radiation source to deliver a 15.0 kGy dose of gamma rays. The irradiation resulted in the formation of microcapsules in which 10–15% of the monomeric albumin was insoluble.

EXAMPLE 5

In the second step of the process of Example 1 or 2 was varied as follows. A small aliquot of the microcapsules (0.5 g) was sealed under argon in a glass vial. The vial was cooled to 4° C. and then irradiated with a $^{60}Co$ gamma radiation source to deliver a 50.0 kGy dose of gamma rays to the microcapsules. Following irradiation, the microcapsules were incubated in oxygen at 50° C. for 6 hours. The irradiation resulted in the formation of microcapsules in which 50–60% of the monomeric rHA was insoluble.

EXAMPLE 6

In the second step of the process of Example 1 or 2 was varied as follows.

A small aliquot of microcapsules (0.5 g) was resuspended in 5 ml of ethanol, chloroform or methylene chloride containing a) 1.5% glutaraldehyde, b) 2.0% diphthaloyl chloride or c) 5.0% formaldehyde. The microcapsules were stirred for varying times from 10 minutes to 3 hours. The microcapsules were removed by filtration and washed thoroughly in the original organic buffer containing 5% ethanolamine, in order to remove excess cross-linking agent. Finally the microcapsules were washed in organic solvent and vacuum dried to remove any residual solvents. The extent of insolubilisation may be varied from 5–100% by this method resulting in the extension of in vitro echogenic half-life from 1–2 minutes to in excess of one hour.

EXAMPLE 7

The two independent steps of microcapsule formation and insolubilisation of the shell may be combined in a single process. In this example, the formation of the microcapsules and the insolubilisation of the polymeric material are achieved simultaneously during the spray drying process.

A solution of rHA was fed by peristaltic pump to a small reaction chamber, with a separate feed line supplying a 5% solution of a suitable crosslinking agent, eg glutaraldehyde, diphthaloyl chloride or formaldehyde. The residence time in the reaction chamber was such that initial adduct formation between the crosslinking agent and the protein was achieved, but intraprotein crosslinking was prevented. The reaction vessel outlet was fed directly to the two fluid nozzle atomisers mounted in a specially adapted spray drying unit, capable of handling volatile solvents. The conditions of spray drying were as outlined in Example 1. The microcapsules were incubated dry at room temperature to allow intraprotein crosslinks to form and then suspended in ethanol containing 5% ethanolamine to quench any remaining crosslinking agent. Thorough washing of the microcapsules was performed and finally the microcapsules were vacuum dried to remove residual solvent.

EXAMPLE 8

Assay of Free Monomeric rHA In Microcapsules

A 1 ml volume of ethanol was added to 100 mg of microcapsules in a 20 ml glass bottle and sonicated for 30 seconds. To this suspension 19 ml of $H_2O$ were added.

The mixture was centrifuged in a bench-top microfuge (Gilson) for 20 seconds and the clear fraction assayed. The assay was performed by loading 50 ml of the fraction automatically onto a Shimadzu LC6A HPLC and chromatographing on a TSK gel permeation column at a flow rate of 1 ml minute$^{-1}$ using sodium phosphate buffer (pH 7.0).

The peak heights representing the rHA monomer were recorded and used to determine the concentration of monomer using a standard curve between 1 and 10 mgml$^{-1}$ monomeric rHA.

The %-free monomeric rHA was calculated by measuring the monomer concentration in the fixed microcapsules and representing this figure as a percentage of the monomer concentration of the unfixed microcapsules. The results are given in FIG. 2.

Heating of the spray dried microcapsules in an oven (as described in Example 1) results in a decrease in the amount of monomer that can be detected (see FIG. 2). This decrease in detectable monomeric rHA is due to the denaturation and crosslinking of monomeric rHA into insoluble polymers that cannot be assayed by the aforementioned HPLC method.

Using the HPLC method to assess rHA monitor levels, it is clear from FIG. 2 that after 15 minutes incubation there is no free monomeric rHA present in the rHA microcapsules. However it is still possible to further crosslink the rHA microcapsules by heating for longer periods.

This prolonged heating results in an increased level of microcapsule crosslinking which in turn produces microcapsules of increasing strength which are correspondingly more resistant to pressure.

By careful control of temperature and time of incubation, it is possible to produce microcapsules with a controlled range of crosslinking (and hence pressure resistivity).

EXAMPLE 9

Figure 3:
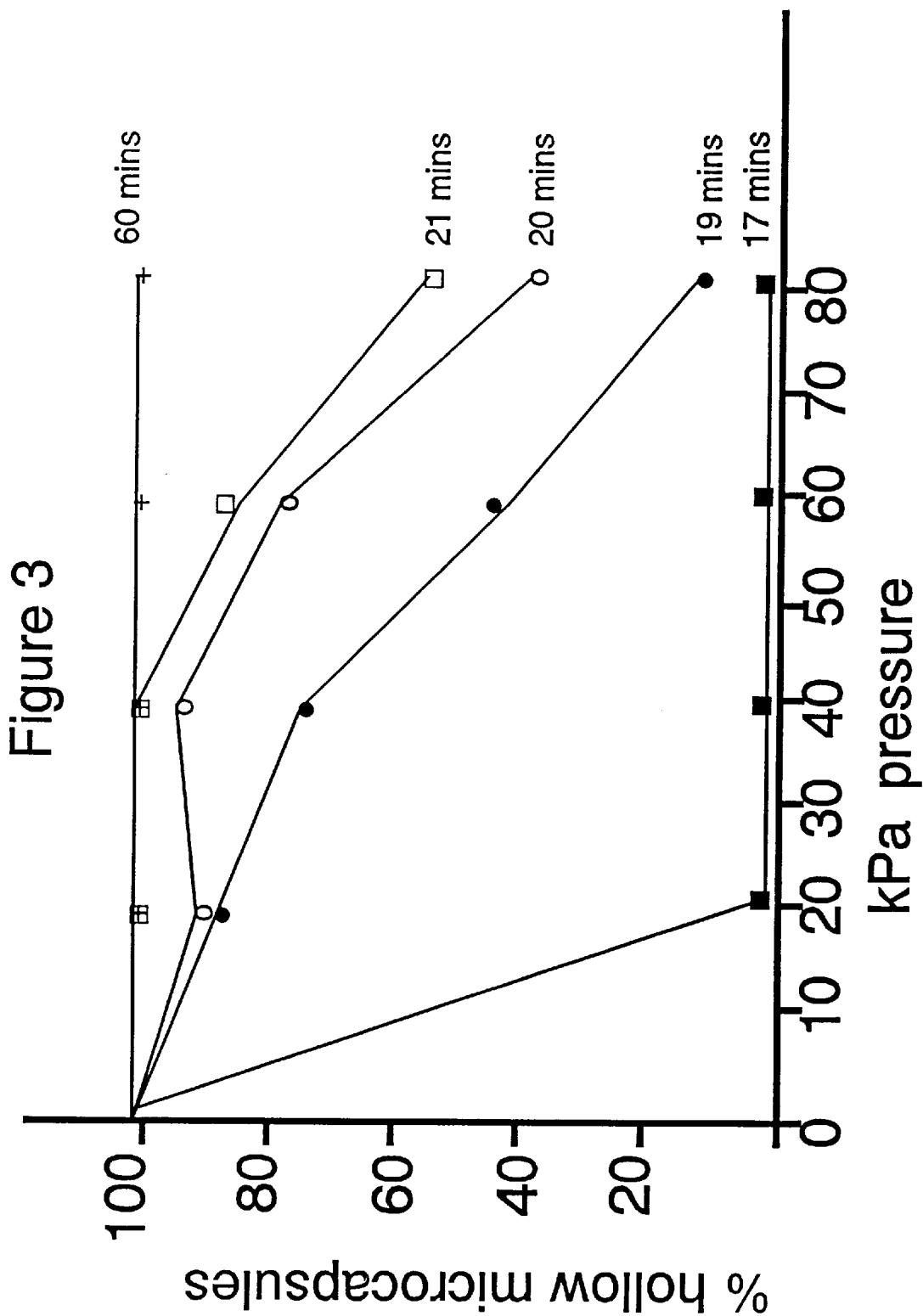

Effects of Incubation Time at 175° C. on the Pressure Resistivity of rHA Microcapsules A batch of rHA microcapsules was divided into 5 g aliquots and baked at 175° C. for varying lengths of time as shown in FIG. 3.

Following heat fixation the amount of free monomer was determined as described in Example 8. For each of the incubations shown, there was no monomeric rHA detectable.

The heat-fixed microcapsules were disaggregated using a Fritsch centrifugal mill (as described above) and intact, air-containing microcapsules recovered by the aforementioned flotation technique. The recovered icrocapsules were suspended in H$_2$O containing Pluronic F68 (1 mgml$^{-1}$) at a concentration of 0.5×10$^8$ capsules ml$^{-1}$.

The resuspended, air-containing microcapsules were subjected to increased atmospheric pressure by applying pressure with a 50 ml syringe whilst containing this suspension in a closed container (25 ml polystyrene container).

For each of the pressures assessed, the individual microcapsule suspension was pressurised to the selected pressure and maintained at this pressure for 5 seconds before releasing the pressure. For each suspension analysed the pressure increase was performed 3 times. The pressure in the closed container was assessed by an RS hand-held manometer.

Following pressurisation the microcapsule suspensions were assessed by light microscopy and image analysis and the % air-containing to non-air-containing microcapsules assessed. This analysis is performed since only the air-containing microcapsules are functional in enhancing ultrasound echocontrast.

As can be seen in FIG. 3, microcapsules that are fixed for 60 minutes at 175° C., as described in Example 1, are stable at all of the pressures to which they were subjected in this experiment.

By careful control of the length of incubation at this articular temperature (175° C.) it is possible to produce batches of microcapsules with different degrees of crosslinking which in turn are resistant to varying degrees of pressure increase.

Using this careful control of crosslinking by adjusting the length and temperature of incubation it is possible to produce batches of air-containing microcapsules that are specifically designed to withstand a designated pressure increase.

The temperature used to crosslink the microcapsules can vary infinitely, as can the length of incubation time.

EXAMPLE 10

Microcapsule Classification

An advantage of the process of the invention is that it enables the median size and size distribution of the microspheres to be controlled. However, one can further select desired sizes if one wishes, for example by flotation. In a homogeneous dispersion of microspheres, larger particles will rise to the surface faster than smaller particles due to the lower density (more encapsulated air) of the larger particles. Hence, by allowing the dispersion to stand, the particle size distribution will change at any level of the solution with respect to time.

Microcapsules were dispersed in 2000 ml of aqueous solution containing 6% w/v sodium chloride and 0.1% w/v Pluronic F68 in a glass bottle giving a liquid column of approximately 165 mm. A sampling tube was placed 50 mm below the upper liquid surface to enable removal of samples at timed intervals.

By altering the standing time and sodium chloride concentration, it was possible to produce a variety of particle size distributions and classify microcapsules down to 2 μm.

Other wet techniques for classification include hydrodynamic chromatography and field flow fractionation. 'Dry' techniques using the principles of elutriation and cross flow separation are commercially available in the form of the Microsplit (British Rem.), Zig-zag (Alpine) and Turbo (Nissuin) classifiers. The elbow jet classifier produced by Nitettsu Mining Co uses a different principle (the Coanda Effect) which could also achieve good results for the classification of microcapsules.

Further Details of Construction of Atomiser

In FIG. 1, reference numeral 1 denotes the feeding device. 2 is a ceiling air disperser which ensures effective control of the air flow pattern. Swirling air is directed around the vaned disc atomiser. 3 is a rotary atomiser or nozzle atomiser. 4 shows a stainless steel interconnecting pipe system which can easily be stripped down for cleaning. 5 are steps for access to the chamber top. 6 is the switch for an air valve for activation of the pneumatic lifting device when raising the chamber lid. 7 is a highly-efficient stainless steel cyclone in which the powder and the exhausted drying air are separated. 8 is a glass jar in which the powder is recovered. 9 is a centrally located instrument panel. 10 is a centrifugal exhaust fan with 3-phase motor. 11 is a damper for air flow control and 12 is an electric air heater which provides drying air temperatures up to 350° C. The drying air temperature can be continuously adjusted using a percentage timer switch. The maximum powder consumption is 7.5 kW.

Evaporative Capacity

| Drying Air | Inlet Air Temperature | Outlet Air Temperature | Evaporative Capacity |
|---|---|---|---|
| 85 kg/h | 150° C. | 80° C. | 1,3 kg/h |
| 85 kg/h | 170° C. | 85° C. | 1,7 kg/h |
| 80 kg/h | 200° C. | 90° C. | 2,5 kg/h |
| 80 kg/h | 240° C. | 90° C. | 3,4 kg/h |
| 75 kg/h | 350° C. | 90° C. | 7,0 kg/h |

Weight and Dimension

| | |
|---|---|
| Weight | 280 kgs |
| Length | 1800 mm |
| Height | 2200 mm |
| Width | 925 mm |

Power

The unit can only be operated on a 3-phase power supply (50 or 60 Hz) at alternative voltages of 440, 415, 400, 380, 220, 200 V.

All parts coming into contact with the liquid or the product are made of acid-resistant, stainless steel AISI 316.

We claim:

1. Sterile hollow microcapsules with proteinaceous walls in which at least 90% of the microcapsules have a diameter in the range 1.0–8.0 $\mu$m; at least 90% of the microcapsules have a wall thickness of 40–500 nm; and at least 50% of the protein in the walls of the microcapsules is so cross-linked as to be resistant to extraction in 1% HCl for 2 mins, wherein said microcapsules are capable of being dried to form a dry powder of said microcapsules.

2. Sterile hollow microcapsules according to claim 1 wherein at least 95% of the protein is cross-linked as said.

3. Sterile hollow microcapsules predominantly of 1.0–10.0 $\mu$m in diameter, at least 10% of the microcapsules, when suspended in water, being capable of surviving a 0.25 s application of a pressure of $2.66\times10^4$ Pa without bursting, collapsing, or filling with water, wherein said microcapsules are capable of being dried to form a dry powder of said microcapsules.

4. A process of forming a stable, sterile powder comprising hollow microcapsules which are suspendable in a medium suitable for parenteral administration to form a suspension suitable for ultrasound imaging when administered parenterally, said process comprising:

(a) providing a solution of a biocompatible and biodegradable wall-forming material in a liquid;

(b) atomizing said solution through an orifice into a heated gas such that said liquid evaporates thereby forming hollow microcapsules of said material having a diameter of from 0.05 to 20 $\mu$m;

(c) heating said microcapsules to fix said microcapsules of step (b), thereby obtaining said microcapsules as a stable powder; and (d) rendering said powder sterile.

5. A process according to claim 4, wherein said biocompatible and biodegradable wall-forming material is protein.

6. A process according to claim 5, wherein said protein is human albumin prepared from serum or by recombinant DNA techniques.

7. A process according to claim 5, wherein said protein solution contains 10.0%–30.0% protein.

8. A process according to claim 5, wherein the hollow microcapsules produced in step (b) are 96–98% monomeric protein.

9. A process according to claim 5, wherein the hollow microcapsules produced in step (c) contain no more than 5% monomeric protein.

10. A process according to claim 5, wherein said protein solution is atomized under conditions such that steps (b) and (c) are carried out substantially simultaneously.

11. Microcapsules obtained by a process according to any one of claims 4–10.

* * * * *